United States Patent [19]
Collins et al.

[11] Patent Number: 5,376,108
[45] Date of Patent: Dec. 27, 1994

[54] ELECTRODE LEAD ANCHORING APPARATUS AND METHOD EMPLOYING DUAL SUTURE COLLARS

[75] Inventors: Kenneth A. Collins, Neutral Bay, Australia; Mark Christensen, Parker, Colo.

[73] Assignee: Telectronics Pacing Systems, Inc., Englewood, Colo.

[21] Appl. No.: 65,258

[22] Filed: May 20, 1993

[51] Int. Cl.5 .............................................. A61N 1/05
[52] U.S. Cl. .................................. 607/115; 607/127; 604/174
[58] Field of Search ............... 607/115, 116, 119, 122, 607/125–132; 128/642; 604/174, 175, 177, 178, 180

[56] References Cited

U.S. PATENT DOCUMENTS

| | | | |
|---|---|---|---|
| 3,046,984 | 7/1962 | Eby | 604/180 |
| 4,516,584 | 5/1985 | Garcia | 607/119 |
| 4,683,895 | 8/1987 | Pohndorf | 604/174 X |
| 5,273,053 | 12/1993 | Pohndorf | 607/132 |

*Primary Examiner*—Lee S. Cohen
*Assistant Examiner*—Jeffrey R. Jastrzab
*Attorney, Agent, or Firm*—Gottlieb, Rackman & Reisman

[57] ABSTRACT

An implantable lead fixation apparatus, including two suture collars connected by a flexible retaining member of predetermined length, is provided for anchoring an elongate cylindrical electrode lead to a patient's body. Each suture collar comprises a flexible annular member having a central lumen that is adapted to enclose the lead. The suture collars each include provision for securing the lead against longitudinal movement of the lead with respect to the collar, and provision for anchoring the collar to the patient's body. The suture collars are positioned relatively proximally and distally with respect to the lead, and are secured on the lead with the proximal suture collar being separated from the distal suture collar by slightly less than the length of the retaining member. Then, the lead fixation apparatus is positioned with respect to the patient's body and secured to the body so that the proximal suture collar is located at a selected distance less than the predetermined distance from, and at an angular orientation to, the distal suture collar to provide slack in both the lead and the retaining member in order to accommodate patient movement without applying dislocating forces to a distal portion of the lead.

19 Claims, 8 Drawing Sheets

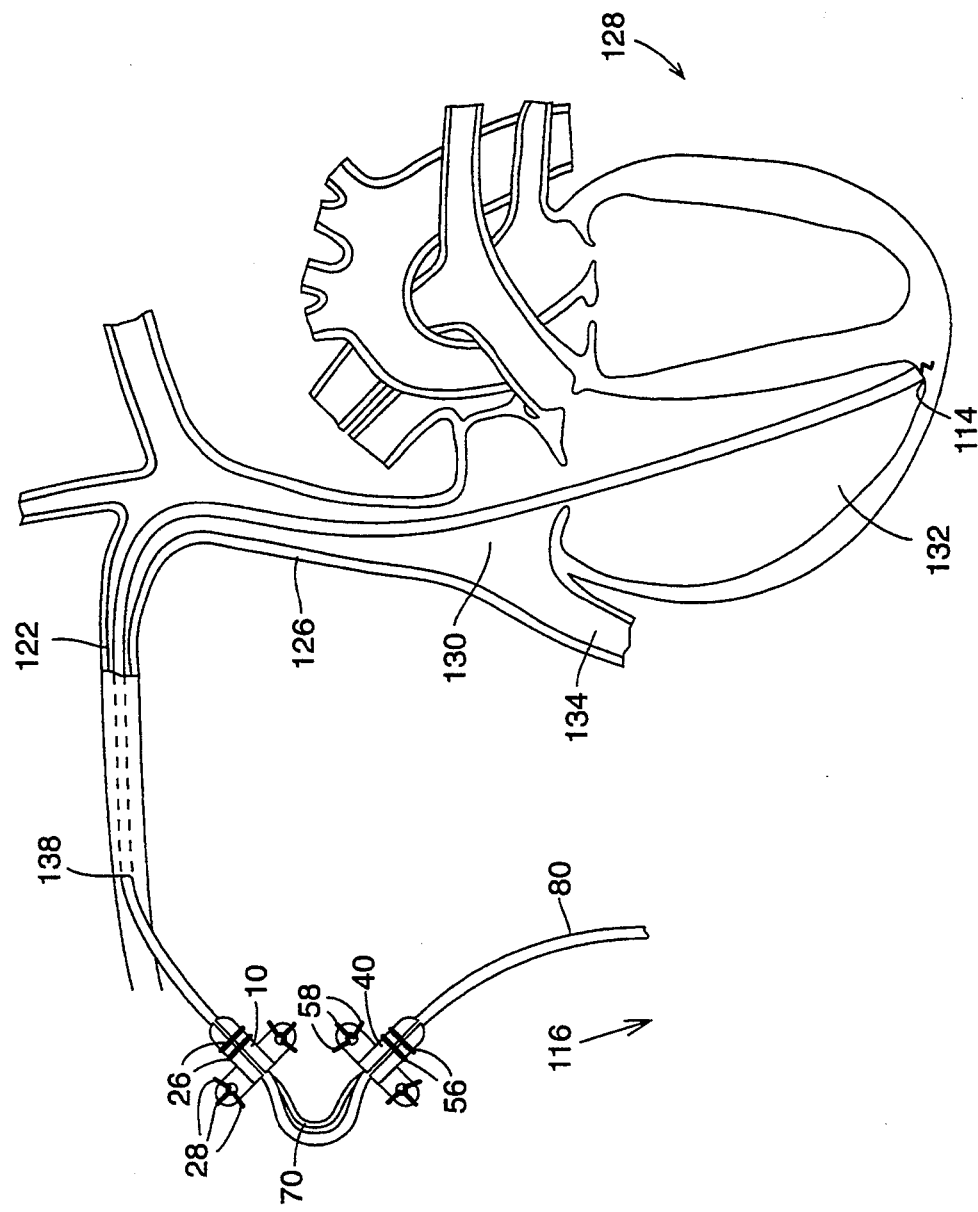

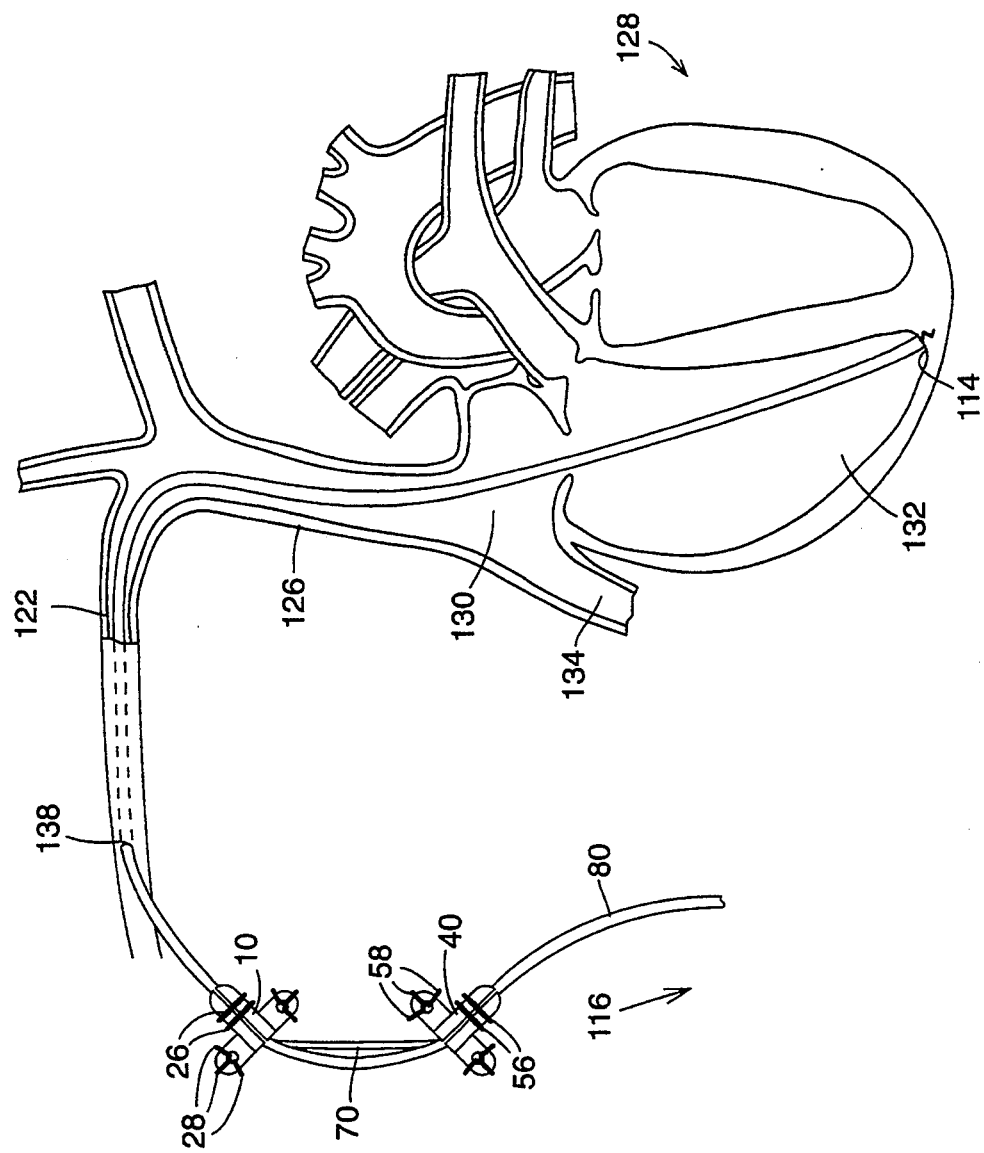

ELECTRODE LEAD ANCHORING APPARATUS AND METHOD EMPLOYING DUAL SUTURE COLLARS

FIELD OF THE INVENTION

The present invention relates to an apparatus and method for anchoring to a patient's body an elongate implanted electrode lead, and more particularly, to such an apparatus and method which relieves patient-movement-generated torsion and traction forces on the lead.

BACKGROUND OF THE INVENTION

Implantable pulse generators are implanted in a formed pocket beneath the skin of a patient. Some pulse generators, such as defibrillators or pacemakers implanted in children, are placed in a pocket formed in the abdominal region of the patient. As is shown in FIG. 1, which illustrates a conventional method of implanting a pulse generator in a patient's torso 120, an electrode lead 80 carries electrical stimulating pulses produced by a pulse generator 110, for example a defibrillator, to a stimulating site 114 on the patient's heart 128. A distal tip portion of the electrode lead is entered into a perforation 138 in a vein (such as the right subclavian vein 122), threaded through the vein and the superior vena cava 126, introduced into the right atrium 130 of the heart 128 and affixed to the stimulating site 114 in the right ventricle 132 of the heart. A proximal end of the lead is tunnelled under the skin from the perforation 138 in the vein 122 to an implantation pocket 115 into which the pulse generator 110 is placed in the patient's abdomen 109. To allow for a patient's common rotation and extension motions occurring during daily life, a clinician will provide some slack in the lead 80 and place the excess lead 80 length in a loop 112 under the patient's skin.

The manner of implantation shown in FIG. 1 has numerous disadvantages. It is well known that an electrode lead tip may dislodge from the heart or that damage may occur to an electrode lead as a result of traction or torsion forces which act upon a lead implanted in this manner. FIGS. 2A and 2B illustrate a conventional lead failure due to kinking. When a patient rotates at the pelvis or extends the upper body, a traction force 116 pulls on and extends the lead 80. The extension of the lead 80 may be sufficient to pull the loop 112 tight, resulting in a kink 118 shown in FIG. 2B. A kink 118 may damage either a conductor internal to the lead or insulation covering the conductor, ruining the functionality of the lead either by decreasing or eliminating the amplitude of a delivered stimulating pulse, destroying the capability of the pulse generator to sense electrical activity of the heart, by causing a significant power drain which shortens the service lifetime of the pulse generator, or by generating an artificial electrical signal (a noise signal) which could be interpreted by the device as a heart signal.

Furthermore, an additional disadvantage of the conventional manner of implanting a lead arises due to the common practice of looping the excess lead length within the body. Looping the excess lead length causes a torsion force to be stored in the lead. Extensions, contractions and flexions of the patient's body place traction forces on the lead which pull and push the lead loops, resulting in changes in the diameter of the loop and the generation of a torque acting on the lead body. FIGS. 3A and 3B illustrate a manner in which traction forces on a lead may result in a propagation of rotational or torsion forces on the lead 80. When a patient contracts the upper body, a compression force 108 may act upon the lead 80 which leads to expansion 119 of the lead loop 112, creating a torque 117 or torsional force which propagates up and down the lead 80. As the lead 80 rotates under such torsional force 117, the lead tip (not shown) will rotate. Over time these forces may tend to cause a helical screw lead tip to unscrew, or may cause other types of fixation devices, such as a tine fixation apparatus, to twist out of position from within the heart.

Although many electrode leads employ coiled wires, which tend to avoid kinking, most lead loops will expand or "pull out" to translate traction forces into torque.

FIG. 4 illustrates an improved conventional manner for implanting an electrode lead 80 which relieves some of the torsion and traction forces on the electrode lead tip at the stimulating site 114 by securing the lead 80 to body tissue near the perforation 138 in the vein into which the lead 80 is inserted. The lead 80 is secured to the body using a suture collar 111, fastened by suture ties 113. The suture collar 111 relieves the torsion and traction forces on the distal tip of the electrode lead 80 at stimulating site 114 merely by transferring and limiting the action of those forces to the location at which the suture collar 111 is placed in the body. These forces are merely moved and not greatly lessened or eliminated. Therefore, the torsion and traction forces will act directly upon the suture collar 111, over time, with the torsion forces tending to weaken the sutures 113 in the circumferential direction and the traction forces pulling and pushing against the sutures in a longitudinal direction. Ultimately, the suture ties 113 may fail and the lead 80 may tear free from the body tissue, nullifying the advantage of securing the lead 80 using the suture collar 111.

What is desired for anchoring an electrode lead to a patient's body, is an apparatus and method which eliminates or greatly reduces the torsion and traction forces acting on the lead. The lead anchoring apparatus and method of the present invention differs from conventional anchoring arrangements by utilizing two interconnected and selectively positioned suture collars to anchor the lead to the patient's body in a manner which reduces or eliminates traction forces that act longitudinally upon the distal portion of the lead.

It follows that the reduction of such torsion and traction forces will prevent dislodging of the lead tip from the heart, since torsion forces tend to unscrew a helical screw lead or twist out tined leads. Furthermore, traction forces weaken the implant by pulling or pushing on the lead tip. In addition, the lead anchoring arrangement of the present invention prevents damage to the lead from kinking, distention or contraction, and prevents dislodging of the suture collar, as well as the implanted lead tip, from the patient's tissue.

SUMMARY OF THE INVENTION

In accordance with a first aspect of the present invention, as embodied and broadly described herein, an implantable fixation apparatus is provided for anchoring to a patient's body an elongate cylindrical electrode lead. The apparatus includes first and second flexible annular suture collars, each having a lumen extending axially therethrough which is adapted to receive the lead therein, and a flexible retaining member of predetermined length which is fixed to each of, and interconnects, the collars. The retaining member serves to limit relative separation of the collars from one another. Each of the suture collars includes a means for securing the collar to the lead to prevent longitudinal movement of the lead with respect to the collar. Additionally, each of the suture collars includes a means for anchoring the collar to the patient's body.

In a preferred embodiment of the invention, the securing means may comprise a plurality of axially spaced circumferential suture grooves formed in an exterior surface of the suture collar to accommodate circumferential sutures tied thereabout for securing the collar to the electrode lead.

In a further embodiment of the invention the electrode lead has a given outside diameter, the lumen has a diameter at least as great as the outside diameter of the lead, and the securing means may each include an axial slot formed in a wall of the suture collar and extending radially from the lumen to the exterior surface of the collar. The slot permits the diameter of the lumen to be decreased to facilitate the securing of the collar to the electrode lead.

In a still further embodiment of the invention, each of the anchoring means comprises a flexible anchoring member having a generally planar surface thereon extending outwardly from the collar to provide a surface for suture-tying the collar to the patient's body. Additionally, the anchoring member may include a pair of spaced apart apertures extending therethrough perpendicular to the planar surface. The apertures are provided to receive sutures therein for tying the anchoring member to the patient's body.

In accordance with a second aspect of the present invention, a lead assembly is provided which is adapted to be implanted in a patient's body. The lead assembly comprises a lead member that further includes a longitudinally elongate conductor covered by an elongate cylindrical insulating sheath. The lead assembly also includes an electrode coupled to the distal end of the conductor, an electrical connector coupled to the proximal end of the conductor and an implantable fixation apparatus in accordance with the aforementioned first aspect of the present invention.

In accordance with a third aspect of the present invention, a method is provided for anchoring to a patient's body an implanted elongate cylindrical electrode lead which includes a distal electrode and a proximal electrical connector, an inner conductor which electrically interconnects the electrode and the connector, and an outer insulation sheath surrounding the conductor. The method comprises the steps of: providing first and second annular suture collars, each collar having a lumen extending therethrough adapted to receive the lead therein, and each collar being fixed to respective ends of a flexible retaining member of predetermined length which serves to limit relative separation of the collars from one another to the predetermined length; inserting a distal portion of the lead through a perforation in a vein leading to the patient's heart to position the electrode in the heart; securing the collars on the lead externally of the vein at spaced apart locations corresponding substantially to the predetermined length; and anchoring the collars to the patient's body at locations spaced apart less than the predetermined distance to provide slack in the lead between the locations, thereby to accommodate patient movement without applying dislocation forces to the distal portion of the lead during such movement. Preferably, the step of anchoring the collars to the patient's body includes a sub-step of orienting the collars so that the longitudinal axes of the collars are approximately perpendicular to one another.

In the preferred practice of the method, the steps of securing the collars on the lead and anchoring the collars to the patient's body are performed by suturing the first and second suture collars both to the lead and to the body.

These and other features of the present invention are depicted in the several embodiments of the invention illustrated in the drawings and described herein.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIG. 8 is a front view of a portion of a human chest, illustrating the human heart with a portion cut away to show the inside thereof, depicting an improved manner in which an electrode lead and pulse generator may be implanted in a patient using the dual suture collar fixation apparatus of the present invention; and FIG. 9 is a front view of a human chest, similar to FIG. 8, showing how the dual suture collar fixation apparatus of the present invention functions under a condition of failure of one of the suture collar ties.

DETAILED DESCRIPTION OF THE INVENTION

Figure 5:
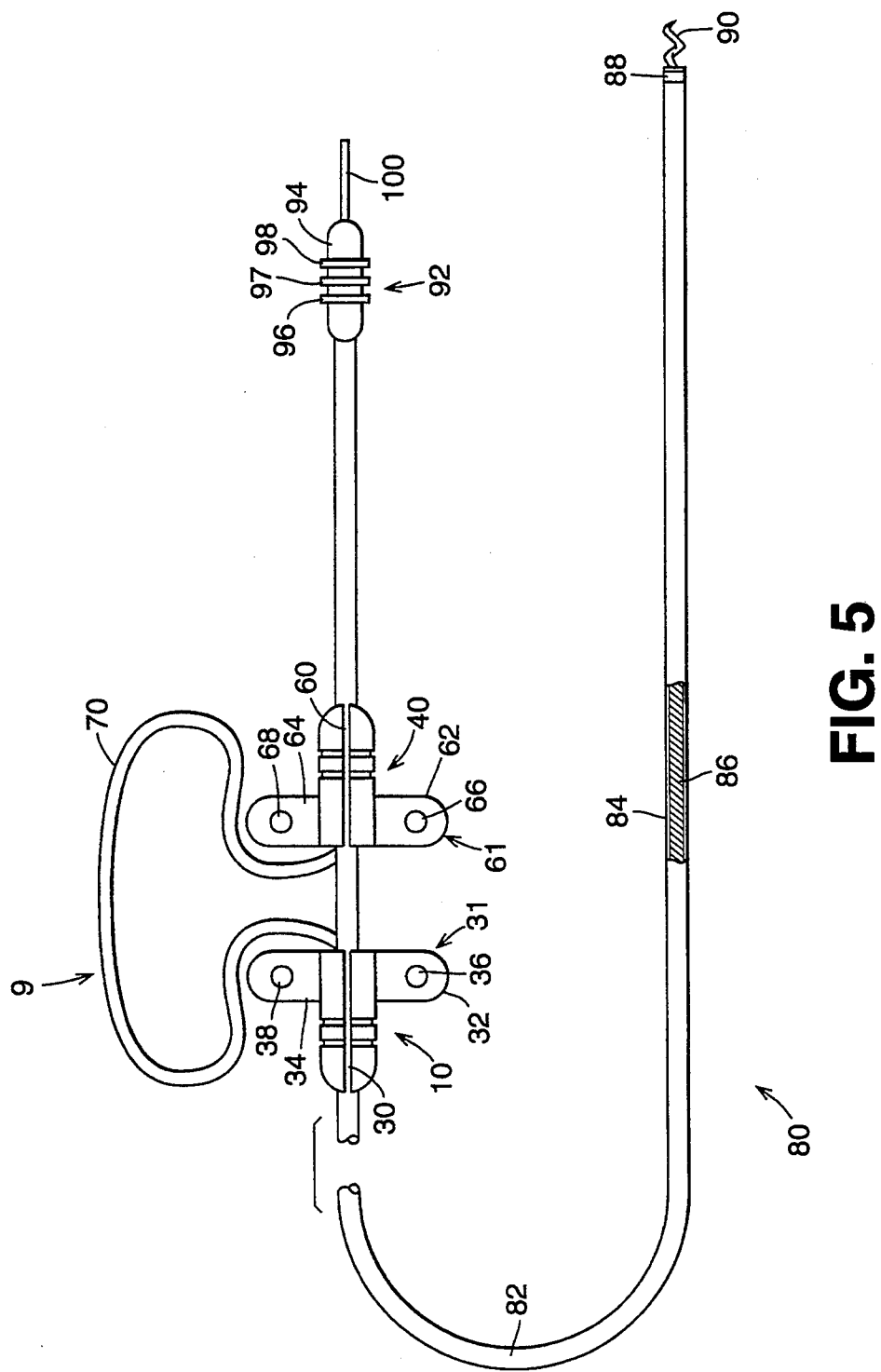
FIG. 5 is a plan view, partially cut away, of an implantable fixation apparatus, in accordance with the present invention, for anchoring to a patient's body an electrode lead, the fixation apparatus including a dual suture collar.
Figure 6:
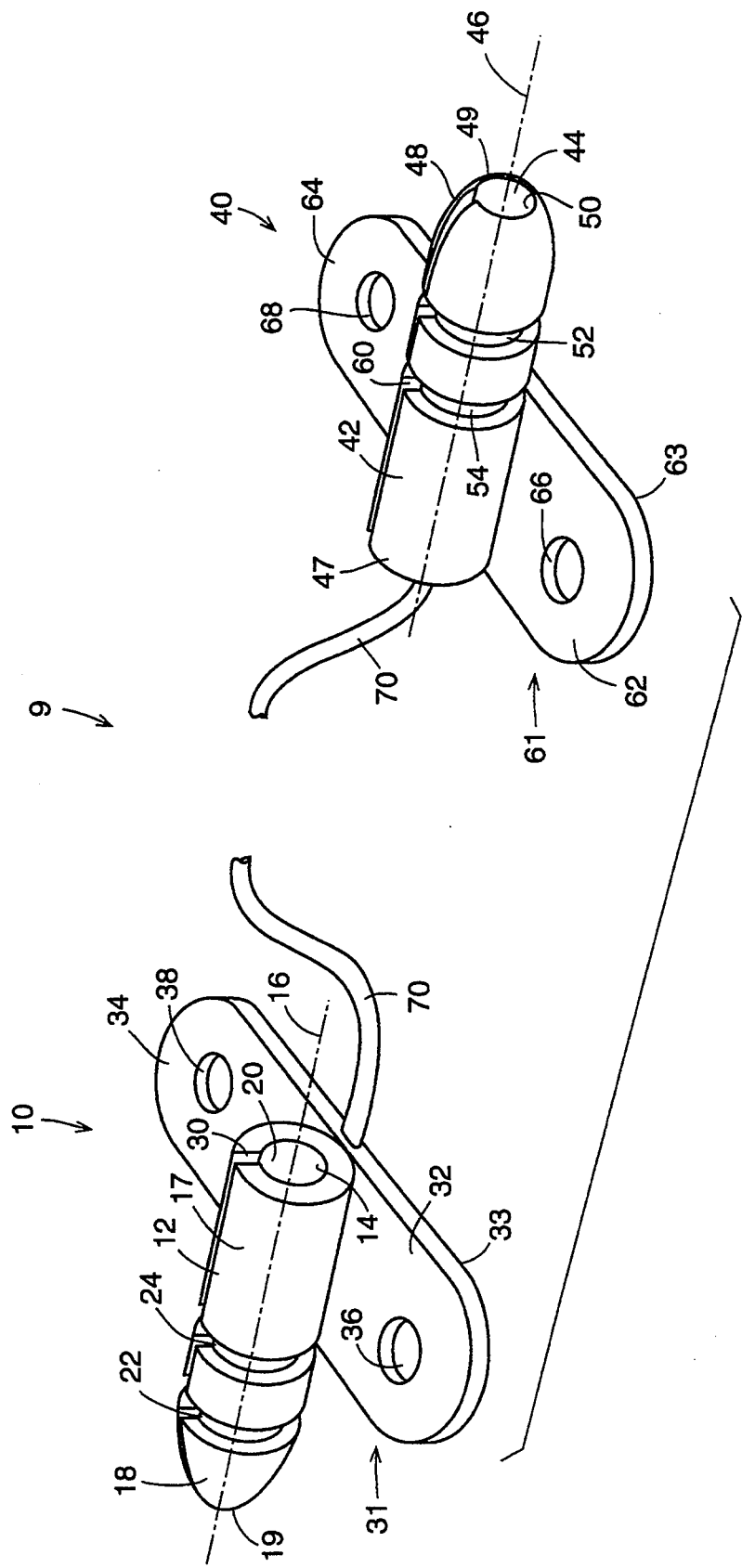
FIG. 6 is an enlarged partial perspective side view of the lead fixation apparatus shown in FIG. 5.
Figure 7:
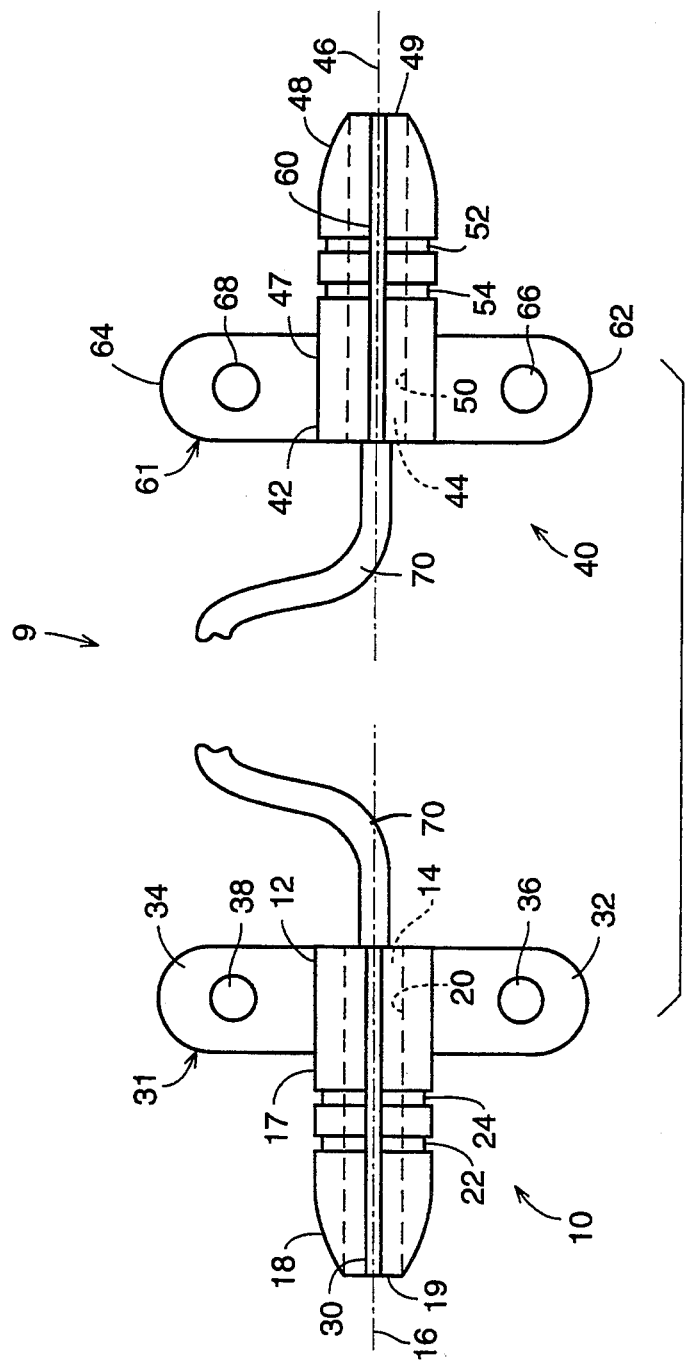
FIG. 7 is a plan view of the lead fixation apparatus shown in FIG. 6.

Reference is now made in detail to the present preferred embodiment of the invention, examples of which are illustrated in FIGS. 5-7 of the accompanying drawings. A dual suture collar fixation apparatus or assembly, shown generally at 9, is slidably mounted upon an electrode lead 80. The fixation apparatus 9 is generally comprised of two suture collars, a distal suture collar 10 and a proximal suture collar 40, which are connected by a flexible retaining member or connecting cord 70.

Referring to FIG. 5 of the drawings, the distal suture collar 10 is an annular member that is separate from but encloses the electrode lead 80. The distal suture collar 10 is firmly affixed to or integral with a means 31 for anchoring the collar 10 to the patient's body. Means 31 includes flexible anchoring tabs 32 and 34 having respective apertures 36 and 38 thereon. Similarly, proximal suture collar 40 is an annular member, which is also separate from but encloses the electrode lead 80. The proximal suture collar 40 is firmly affixed to or integral with a means 61 for anchoring the collar 40 to the patient's body. Means 61 includes flexible anchoring tabs 62 and 64 having respective apertures 66 and 68 therein.

The flexible retaining member or connecting cord 70 is secured at one of its ends to the distal suture collar 10 and at the other of its ends to the proximal suture collar 40. Retaining member 70 interconnects the collars 10 and 40 and limits relative separation of the collars from one another, while allowing the collars to be oriented at a selected angle to one another. For standard electrode leads, the length of the flexible retaining member 70 preferably ranges from about 5 cm to about 20 cm. In the preferred embodiment of the invention, the proximal suture collar 40 is a mirror image of the distal suture collar 10.

The electrode lead 80 is an elongate cylindrical structure having a given outside diameter and comprising a main lead body 82 having a proximal end and a distal end and having an outer insulating sheath 84, composed of a body-compatible polyurethane or silicon rubber, covering an inner conductive coil 86. The inner conductive coil 86 is physically and electrically coupled to at least one electrode 88 at the distal end of the lead 80. Although the lead 80 is shown in FIG. 5 as a single electrode, unipolar lead for simplicity, the description of the invention is easily extended to bipolar leads, defibrillator leads or other standard leads in the art of physiological and biological stimulation. The electrode lead 80 includes a fixation means 90 for attaching the lead 20 to the heart in the vicinity of the electrode 88. The fixation means 90 is depicted in the form of a helical fixation coil but may also take the form of any known active or passive fixation mechanism, including tines, hooks or patches.

Affixed to its proximal end, the electrode lead 80 includes an electrical connector assembly 92 having an insulating outer body 94, sealing rings 96, 97 and 98 and a terminal pin 100, which comprises an electrically conducting metallic member that is electrically coupled to the inner conductive coil 86. The insulating outer body 94 and the sealing rings 96, 97 and 98 electrically insulate the inner conductive coil 86, and prevent biological fluids from coming into contact with the coil 86 to protect the electrical integrity of the electrode lead 80.

Figure 1:
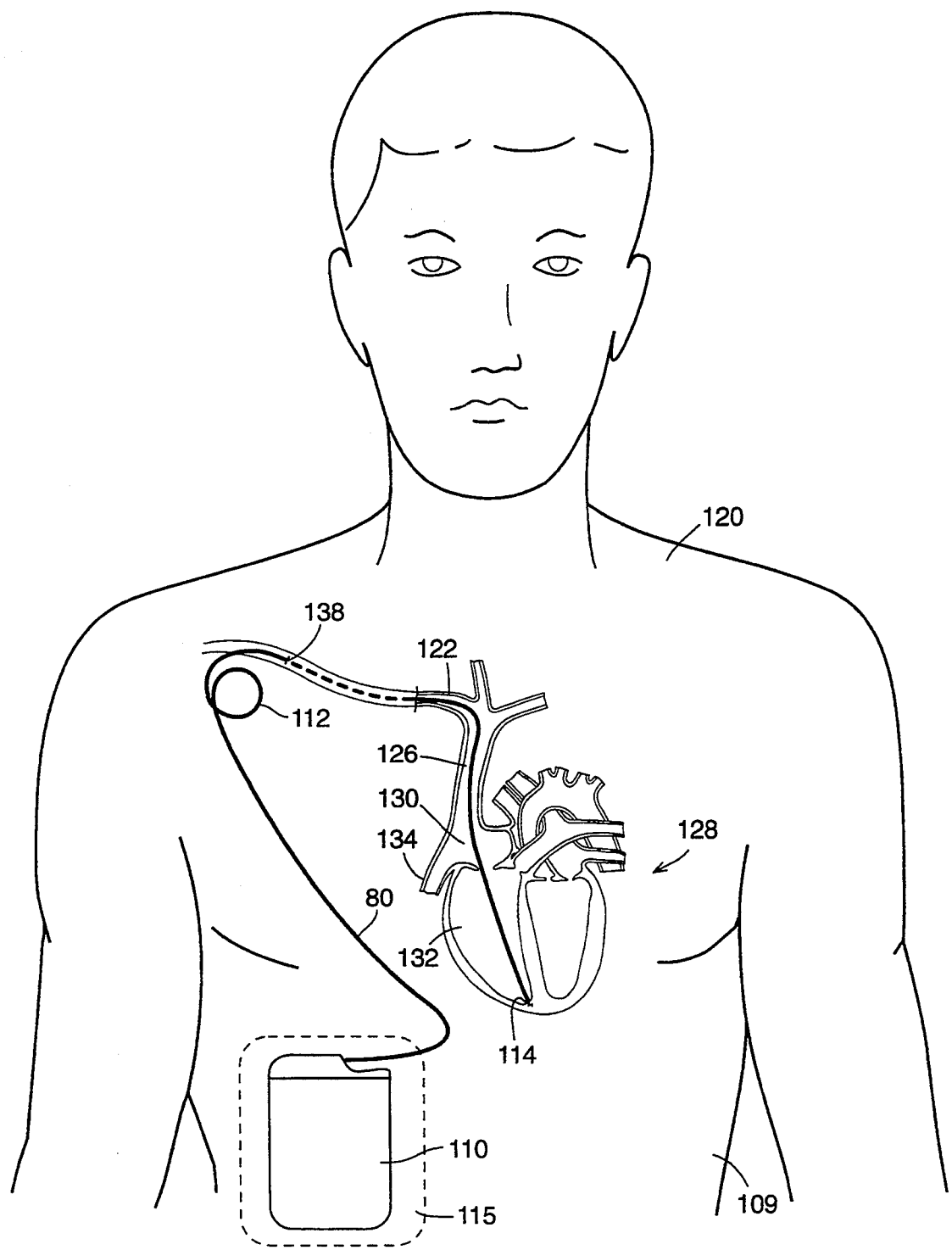
FIG. 1 is a front view of a human torso illustrating the human heart with a portion cut away to show the inside thereof, particularly depicting a conventional manner in which an electrode lead and pulse generator are implanted in a patient.
Figure 2A:
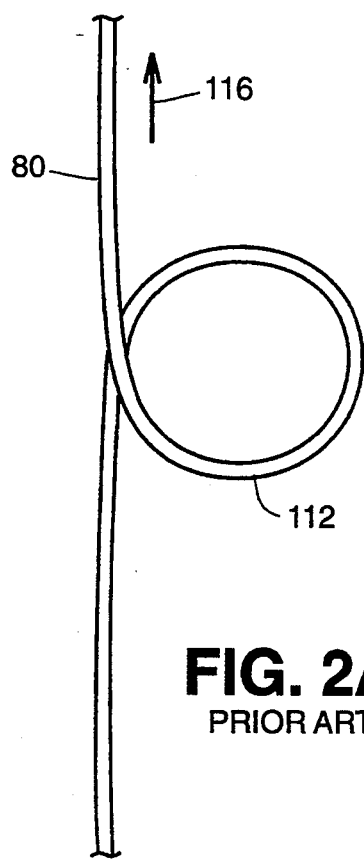
FIGS. 2A and 2B are schematic representations of an electrode lead illustrating a lead failure due to kinking, which may occur when a lead and pulse generator are implanted in the conventional manner shown in FIG. 1.
Figure 2B:
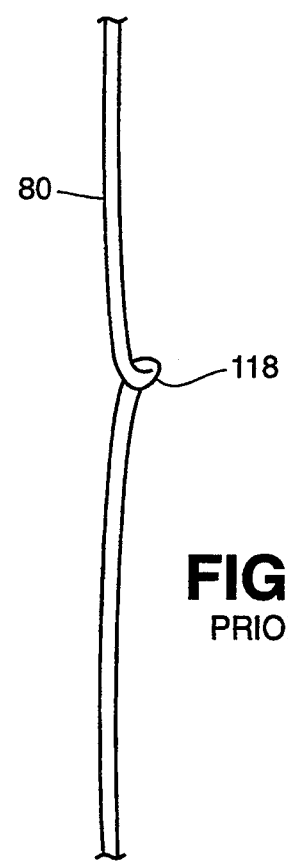
Figure 3A:
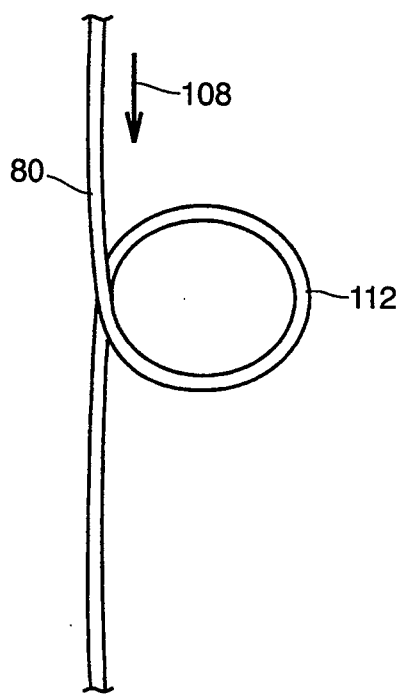
FIGS. 3A and 3B are schematic representations of an electrode lead illustrating a lead failure due to torsion, which may occur when a lead and pulse generator are implanted in the conventional manner shown in FIG. 1.
Figure 3B:
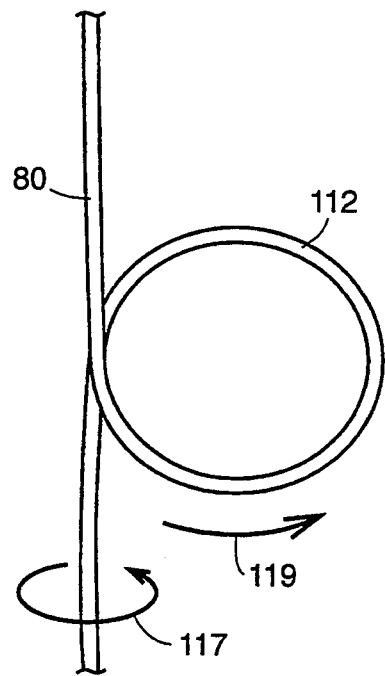

The dual suture collar fixation assembly 9 may slide along the electrode lead 80, from the electrical connector assembly 92 to the electrode 88, so that the assembly 9 may be positioned along the lead 80 in an appropriate position with respect to the body to reduce torsion and traction forces on the lead 80. In an implant (see FIG. 1) in which a pulse generator 110 is implanted in the abdomen and the stimulating site 114 is in the heart 128, the dual suture collar fixation assembly 9 is usually positioned near the perforation 138 in blood vessel 122 into which the lead 80 is advanced.

Referring now to FIGS. 6 and 7, the distal suture collar 10 comprises an annular member or sleeve 12 having a central lumen 14 along its longitudinal axis 16. The sleeve 12 is preferably composed of a medical grade biocompatible silicon, polyurethane or other flexible, bio-compatible low compression material or combination of materials. The central lumen 14 is defined by an interior cylindrical surface 20, having a generally constant diameter that is coaxial with the longitudinal axis 16. The diameter of surface 20 (and, therefore, of lumen 14) may range in size from slightly less than to about 0.35 mm larger than the outside diameter of electrode lead 80. Preferably, the diameter of surface 20 is at least as great as the outside diameter of lead 80.

In a preferred form of the distal suture collar 10, an exterior cylindrical surface 17 of the sleeve 12 is formed so that the distal end of the surface 17 contains a taper 18 which ends in a distal end surface 19. In the exterior cylindrical surface 17 of the sleeve 12 is formed a circumferential groove 22 and a circumferential groove 24. These circumferential grooves are longitudinally spaced from one another along the outer surface 17 of the distal suture collar 10 and are sized to accommodate circumferential suture threads 26, as shown in FIGS. 8 and 9. Again referring to FIGS. 6 and 7, collar 10 is provided with a longitudinally elongate slot 30 that extends throughout the entire length of the sleeve 12, and extends radially through the thickness of the annular wall of the sleeve 12. Thus, the sleeve 12 may be resiliently spread at the longitudinal slot 30 to receive and enclose therein the electrode lead 80. The suture threads 26, grooves 22 and 24, and slot 30, together, comprise a securing means for securing the distal suture collar 10 upon the electrode lead 80 to prevent longitudinal moment of the lead 80 with respect to the collar 10. This is achieved by circumferentially tightening the suture threads 26 to cause the diameter of the lumen 14 to decrease and cause the inner surface 20 of the collar to firmly grasp the lead 80.

The flexible anchoring tabs 32 and 34 of anchoring means 31, in turn, provide for a secure fixation of the collar 10 to the patient's body tissue. Apertures 36 and 38 of tabs 32 and 34, respectively, allow threading of suture threads 28 (see FIG. 8 and FIG. 9) therethrough to affix the collar 10 to the patient's tissue. Preferably, the anchoring means 31 is provided with a planar undersurface 33 which abuts against the patient's body tissue when the anchoring means is fastened to the patient's body by suture threads 28.

Note that one means (22, 24, 26 and 30) is provided for securing the suture collar 10 to the electrode lead 80 and a second means (28, 31, 32, 34, 36 and 38) is provided for securing the suture collar 10 to the patient's tissue. It is important that the attachment of the collar to the lead be separate from the attachment of the collar to the patient's tissue. Otherwise, if the collar, lead and tissue are secured using a single suture tie, forces acting on the lead over time will tend to cause the suture to cut through body tissue and loosen the attachment of the collar to both the patient's tissue and the lead, allowing the collar to thereafter slide along the lead. Thus, the forces on the lead and the motion of the lead will magnify, ultimately causing impairment or failure of the electrical attachment of the lead to the heart.

Like the distal suture collar 10, the proximal suture collar 40 is an annular member or sleeve 42 having a central lumen 44 along its longitudinal axis 46. The sleeve 42 is preferably constructed from a medical grade biocompatible silicon, polyurethane or other flexible, bio-compatible low compression material. The lumen 44 is defined by an interior cylindrical surface 50, having a generally constant diameter that is coaxial with the longitudinal axis 46. The diameter of surface 50 (and, thus, of lumen 44) may range in size from slightly less than to about 0.35 mm larger than the outside diameter of electrode lead 80. Preferably, the diameter of surface 50 is at least as great as the outside diameter of lead 80.

An exterior cylindrical surface 47 of the sleeve 42 is formed so that the proximal end of the surface 47 contains a taper 48 which ends in a proximal end surface 49. In the exterior cylindrical surface 47 of the sleeve 42 are formed circumferential grooves 52 and 54. These circumferential grooves are longitudinally spaced from one another along the outer surface 17 of the proximal suture collar 40 and are sized to accommodate circumferential suture threads 56, as shown in FIGS. 8 and 9.

Returning in reference to FIGS. 6 and 7, collar 40 is provided with a longitudinally elongate slot 60 that extends throughout the entire length of the sleeve 42, and extends radially through the thickness of the annular wall of the sleeve 42. Thus the sleeve 42 may be flexibly spread at the longitudinal slot 60 to receive and enclose therein the electrode lead 80. The suture threads 56, grooves 52 and 54, and slot 60, together, comprise a securing means for securing the proximal suture collar 40 upon the electrode lead 80 to prevent longitudinal movement of the lead 80 with respect to the collar 40.

The flexible anchoring tabs 62 and 64 of anchoring means 61, in turn, provide for a secure fixation of the collar 40 to the patient's body tissue. Apertures 66 and 68 of tabs 62 and 64, respectively, allow threading of suture threads 58 (see FIG. 8 and FIG. 9) therethrough to affix the collar 40 to the patient's tissue. Preferably, the anchoring means 61 is provided with a planar undersurface 63 which abuts against the patient's body tissue when the anchoring means is fastened to the patient's body by suture threads 58.

Figure 4:
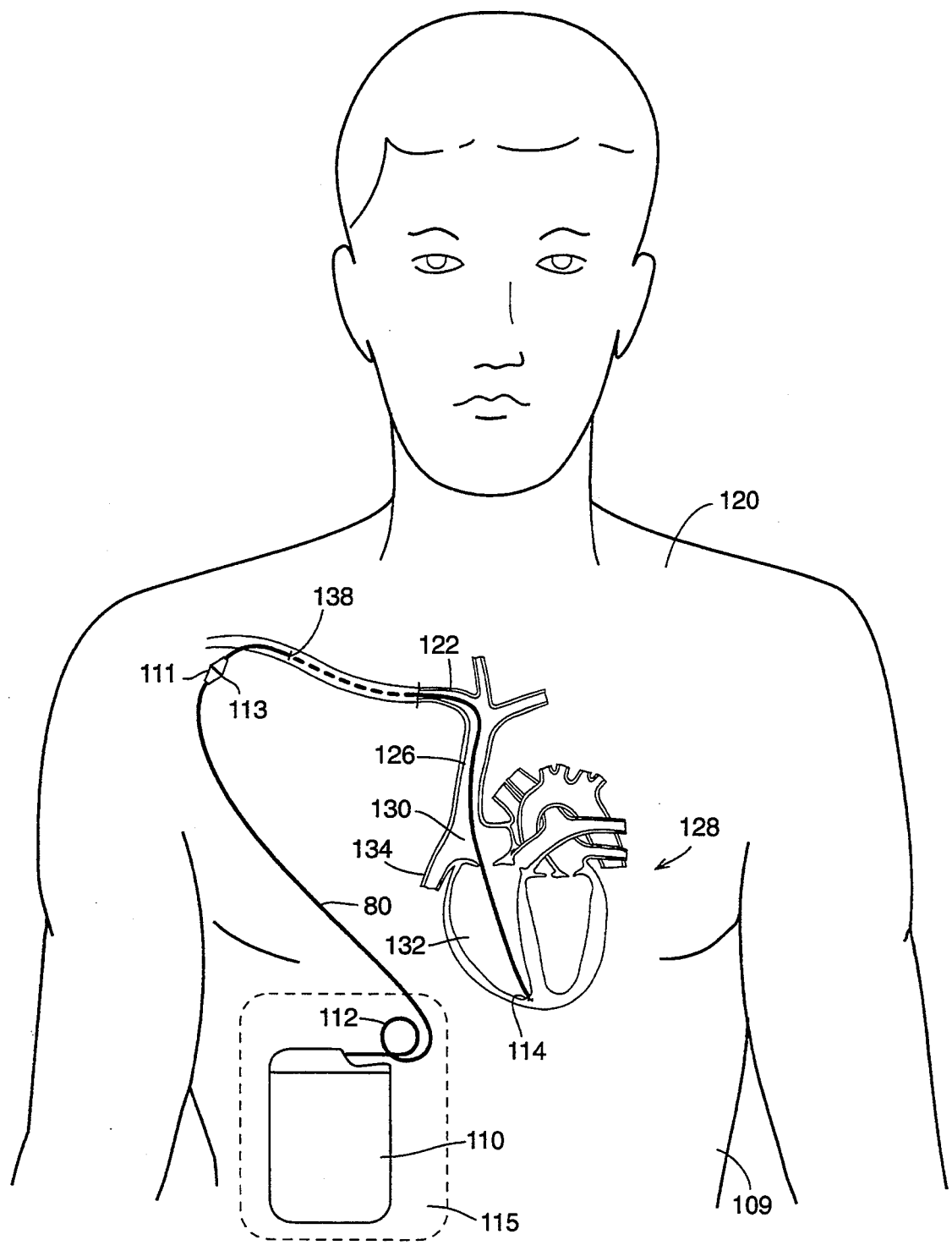
FIG. 4 is a front view of a human torso illustrating the human heart with a portion cut away to show the inside thereof, particularly depicting an improved conventional manner in which an electrode lead and pulse generator are implanted in a patient and in which the lead is affixed to the patient's body using a suture collar.

Referring now to FIG. 8 in conjunction with FIGS. 6 and 7, the electrical stimulating electrode lead 80 is implanted by perforating at 138 a patient's right subclavian vein 122, entering the distal tip of the electrode lead 80 into the perforation 138, threading the lead so through the vein and the superior vena cava 126, introducing the lead into the right atrium 130 of the heart 128 and affixing the tip of the lead 80 to a stimulating site 114 on the heart. The proximal end of the electrode lead 80 is then tunnelled under the skin from the perforation 138 in the vein 122 to the implantation pocket 115 into which the pulse generator 110 (see FIG. 1 or FIG. 4) is placed in the patient's abdomen 109. Next the proximal suture collar 40 and the distal suture collar 10 are secured to the electrode lead 80 by tying the suture threads 56 and 26 into the respective circumferential grooves 52, 54 and 22, 24 of the sleeves 42 and 12, respectively. The distal suture collar 10 is first positioned upon the electrode lead 80 near the venous entry point, the perforation 13e of the right subclavian vein 122. The circumferential suture threads 26 are inserted into the cylindrical grooves 22 and 24 of the distal suture collar cylindrical sleeve 12 at this location and the suture threads 26 are firmly tied so that the distal suture collar 10 cannot slide upon the electrode lead 80. The proximal suture collar 40 is then positioned upon and fastened to the electrode lead 80 at slightly more than the length of the flexible connecting cord 70 away from the distal suture collar 10 so that a small amount of slack will remain in the portion of the lead between the collars 10 and 40 when the cord is fully extended. In fastening collar 10 to the lead 80 the circumferential suture threads 26 are inserted into the cylindrical grooves 22 and 24 of the distal suture collar cylindrical sleeve 12 at this location and the suture threads 26 are firmly tied so that the distal suture collar 10 cannot slide upon the electrode lead 80. The sutures 26 are tied around the circumferential grooves 22 and 24 in order to decrease the width of the longitudinal slot 30 and firmly secure the distal suture collar 10 upon the electrode lead 80. Similarly, the sutures 56 are tied around the circumferential grooves 52 and 54 of suture collar 40 in order to decrease the width of the longitudinal slot 60 and firmly secure the proximal suture collar 40 upon the electrode lead 80. The longitudinal slots 30 and 60 facilitate a secure interlock between the collars and the lead.

The distal suture collar 10 is then secured to the patient's tissue at a position near the venous entry point, the perforation 138 of the right subclavian vein 122, by applying suture ties 28 through the apertures 36 and 38 of the flexible plastic anchoring tabs 32 and 34, respectively. Next, the proximal suture collar 40 is positioned and secured so that the electrode lead 80 extends with a slack-providing U-shape between the proximal suture collar 40 and the distal suture collar 10. The proximal suture collar 40 is oriented at a predetermined angle with respect to the distal suture collar 10 in connection with insuring that this slack in the lead 80 is initially, and remains, essentially stress free. In the preferred embodiment of the fixation apparatus 9, the proximal suture collar 40 is placed at approximately a 90 degree angle with respect to the distal suture collar 10.

In this manner, the electrode lead 80 is firmly secured at two points upon the patient's body, with the two securing collars set at a 90 degree angle to one another to resist traction forces in two directions. In addition, a predetermined length of slack in the electrode lead 80 is stored between the two fixation points. This amount of slack is selected to allow for common rotation and extension motions which occur during a patient's daily life. Further, the dual suture collar fixation apparatus 9 resists movement of the lead which tends to expand and contract loops in the lead that impart rotational motions on the lead and result in the creation of torsion forces along the lead. Thus, the suture collar fixation apparatus of the present invention resists rotation of the lead caused by body movements.

FIG. 9 illustrates an additional advantage of the dual suture collar fixation apparatus 9 of the present invention, i.e., its operation under a condition of failure of the suture collar ties. If a traction force 116 is applied to the lead 80 which causes the suture ties 58 of the proximal suture collar 40 to fail, then the electrode lead 80 and suture collar 40 must be pulled through the length of the flexible connecting cord 70 before a strain is placed on the distal suture collar 10 and the latter, in turn, prevents the strain from acting on the distal portion of the lead 80. Thus the dual suture collar fixation apparatus 9 further helps to prevent dislodging of the lead from the heart.

It will be apparent from the foregoing discussion that the dual suture collar fixation apparatus and electrode lead arrangement of the present invention provide resistance to torsion and traction forces and greatly assist in preventing dislodging of the lead from the heart and damage to the lead.

While a particular embodiment of this invention has been shown and described, it will be obvious to those skilled in the art that various modifications and variations may be made without departing from this invention in its broader aspects. It is, therefore, intended in the appended claims to cover all such modifications and variations as fall within the true spirit and scope of this invention.

What is claimed is:

1. An implantable fixation apparatus for anchoring to a patient's body an elongate cylindrical electrode lead, said fixation apparatus comprising:

first and second flexible annular suture collars, each of said suture collars having a lumen extending axially therethrough, said lumen being adapted to receive the lead therein;

a flexible retaining member of predetermined length fixed to each of said first and second suture collars and interconnecting said collars, said retaining member serving to limit relative separation of said collars from one another to said predetermined length;

respective means on each of said suture collars for securing said collars to the lead to prevent longitudinal movement of the lead with respect to said collars; and respective means on each of said collars for anchoring said collars to the patient's body.

2. An apparatus in accordance with claim 1, wherein each of said securing means comprises a plurality of axially spaced circumferential suture grooves formed in an exterior surface of said suture collar, said circumferential suture grooves being adapted to accommodate circumferential sutures tied thereabout for securing the suture collar to the electrode lead.

3. An apparatus in accordance with claim 2, wherein said electrode lead has a given outside diameter and said lumen has a diameter at least as great as the outside diameter of said lead, and wherein each of said securing means further comprises a longitudinally elongate slot formed in a wall of said suture collar and extending radially from said lumen to said exterior surface of said collar, said slot permitting the diameter of the lumen to be decreased to facilitate the securing of the collar to the electrode lead.

4. An apparatus in accordance with claim 3, wherein said anchoring means comprises a flexible anchoring member having a generally planar surface thereon extending outwardly from said collar to provide a surface for suture-tying said collar to the patient's body.

5. An apparatus in accordance with claim 3, wherein said anchoring means comprises a flexible anchoring member having a generally planar surface thereon extending outwardly from said suture collar and being adapted to provide a surface for suture-tying said suture collar to the patient's body, said anchoring means having a pair of spaced apart apertures extending therethrough, said apertures being perpendicular to the plane of said surface and being adapted to receive sutures for tying said anchoring member to the patient's body.

6. An apparatus in accordance with claim 1, wherein said anchoring means comprises a flexible anchoring member having a generally planar surface thereon and extending outwardly from said collar to provide a surface for suture-tying said collar to the patient's body.

7. An apparatus in accordance with claim 1, wherein said anchoring means comprises a flexible anchoring member having a generally planar surface thereon extending outwardly from said suture collar and being adapted to provide a surface for suture-tying said suture collar to the patient's body, said anchoring member having a pair of spaced apart apertures extending therethrough, said apertures being perpendicular to the plane of said surface and being adapted to receive sutures for tying said anchoring member to the patient's body.

8. A lead assembly adapted to be implanted in, and anchored to, a patient's body, comprising:

a lead member further comprising a longitudinally elongate conductor having a proximal end and a distal end, and an elongate cylindrical insulating sheath having a given outside diameter covering said conductor from its proximal end to its distal end;

an electrode coupled to the distal end of said conductor;

an electrical connector coupled to the proximal end of said conductor; and a lead fixation means for anchoring said lead member to the patient's body, said lead fixation means further comprising:

proximal and distal flexible annular suture collars longitudinally positionable on said lead member, each of said suture collars having a central lumen extending coaxially therethrough, said lumen having an internal diameter at least as great as the outside diameter of said insulating sheath and being adapted to receive said lead member therein;

respective means for securing said lead member to said suture collars to prevent longitudinal movement of said lead member with respect to said collars;

means for anchoring each of said suture collars to the patient's body; and a flexible retaining member of predetermined length fixed to each of said suture collars and interconnecting said collars, said retaining member serving to limit relative separation of said collars from one another to said predetermined length.

9. A lead in accordance with claim 8, wherein each of said securing means comprises a plurality of axially spaced circumferential suture grooves formed in an exterior surface of said suture collar, said circumferential suture grooves being adapted to accommodate circumferential sutures tied thereabout for securing the suture collar to the lead member.

10. A lead in accordance with claim 9, wherein each of said securing means further comprises a longitudinally elongate slot formed in a wall of said suture collar and extending radially from said lumen to said exterior surface of said collar, said slot permitting the diameter of the lumen to be decreased to facilitate securing the collar to the lead member therein.

11. A lead in accordance with claim 10, wherein said anchoring means comprises a flexible anchoring member having a generally planar surface thereon extending outwardly from said suture collar to provide a surface for suture-tying said suture collar to the patient's body.

12. A lead in accordance with claim 10, wherein said anchoring means comprises a flexible anchoring member having a generally planar surface thereon extending outwardly from said suture collar and being adapted to provide a surface for suture-tying said suture collar to the patient's body, said anchoring member having a pair of spaced apart sutures extending therethrough, said apertures being perpendicular to the plane of said surface and being adapted to receive sutures for tying said anchoring member to the patient's body.

13. A lead in accordance with claim 8, wherein said anchoring means comprises a flexible anchoring member having a generally planar surface thereon extending outwardly from said suture collar to provide a surface for suture-tying said collar to the patient's body.

14. A lead in accordance with claim 8, wherein said anchoring means comprises a flexible anchoring member having a generally planar surface thereon extending outwardly from said suture collar and being adapted to provide a surface for suture-tying said suture collar to the patient's body, said anchoring member having a pair of spaced apart apertures extending therethrough, said apertures being perpendicular to the plane of said surface and being adapted to receive sutures for suture-tying said anchoring member to the patient's body.

15. A method for anchoring to a patient's body an implanted elongate, cylindrical electrode lead, said lead including a distal electrode and a proximal electrical connector, said lead having an inner conductor which electrically interconnects the electrode and the connector and having an outer insulation sheath surrounding said conductor, said method comprising the steps of:
providing first and second annular suture collars, each collar having a lumen extending therethrough adapted to receive the lead therein, and each collar being fixed to respective ends of a flexible retaining member of predetermined length which serves to limit relative separation of the collars from one another to said predetermined length;
inserting a distal portion of the lead through a perforation in a vein leading to the patient's heart to position the electrode in the heart;
securing said collars on said lead externally of said vein at spaced apart locations corresponding substantially to said predetermined length; and
anchoring said collars to the patient's body at locations spaced apart less than said predetermined length to provide slack in said lead between said locations, thereby to accommodate patient movement without applying dislocation forces to the distal portion of said lead during such movement.

16. A method in accordance with claim 15, wherein said step of securing the collars on the lead includes a sub-step of suturing the collars to the lead.

17. A method in accordance with claim 16, wherein said step of anchoring the collars to the patient's body includes a sub-step of suturing the collars to the body.

18. A method in accordance with claim 17, wherein said suture collars have longitudinal axes and are longitudinally elongate, wherein said first suture collar is secured to said lead at a relatively distal location thereon and said second suture collar is secured to said lead at a relatively proximal location thereon, and wherein said step of anchoring the collars to the patient's body includes a sub-step of orienting said collars so that the longitudinal axes of said collars are approximately perpendicular to one another.

19. A method in accordance with claim 15, wherein said suture collars are longitudinally elongate, wherein said first suture collar is secured to said lead at a relatively distal location thereon and said second suture collar is secured to said lead at a relatively proximal location thereon, and wherein said step of anchoring the collars to the patient's body includes a sub-step of orienting the collars so that the collars are approximately perpendicular to one another.

* * * * *